(12) United States Patent
Fukasawa

(10) Patent No.: US 10,537,482 B2
(45) Date of Patent: Jan. 21, 2020

(54) ABSORBENT ARTICLE

(71) Applicant: UNICHARM Corporation, Ehime (JP)

(72) Inventor: Jun Fukasawa, Kagawa (JP)

(73) Assignee: UNICHARM CORPORATION, Ehime (JP)

( * ) Notice: Subject to any disclaimer, the term of this patent is extended or adjusted under 35 U.S.C. 154(b) by 229 days.

(21) Appl. No.: 15/129,415

(22) PCT Filed: Jan. 20, 2015

(86) PCT No.: PCT/JP2015/051379
§ 371 (c)(1),
(2) Date: Sep. 26, 2016

(87) PCT Pub. No.: WO2015/146245
PCT Pub. Date: Oct. 1, 2015

(65) Prior Publication Data
US 2017/0112683 A1    Apr. 27, 2017

(30) Foreign Application Priority Data
Mar. 27, 2014  (JP) .................. 2014-066020

(51) Int. Cl.
*A61F 13/15* (2006.01)
*A61F 13/49* (2006.01)
*A61F 13/84* (2006.01)

(52) U.S. Cl.
CPC .... *A61F 13/49061* (2013.01); *A61F 13/4902* (2013.01); *A61F 13/49011* (2013.01);
(Continued)

(58) Field of Classification Search
CPC .......... A61F 13/49061; A61F 13/49011; A61F 13/4902; A61F 13/84; A61F 2013/49033; A61F 2013/8497
(Continued)

(56) References Cited

U.S. PATENT DOCUMENTS

2004/0243083 A1* 12/2004 Matsuda ........... A61F 13/49011
604/385.01
2007/0208316 A1    9/2007 Nakahata et al.
(Continued)

FOREIGN PATENT DOCUMENTS

CN    102871802 A    1/2013
JP    2002-272783 A    9/2002
(Continued)

OTHER PUBLICATIONS

International Search Report in PCT Application No. PCT/JP2015/051379, dated Apr. 21, 2015.
(Continued)

*Primary Examiner* — Jacqueline F Stephens
(74) *Attorney, Agent, or Firm* — Hauptman Ham, LLP

(57) ABSTRACT

An absorbent article includes: an absorbent main, an abdominal-side band member having a central portion fixed to one end part in a vertical direction of the absorbent main body while covering the one end part from a non-skin side of the absorbent main body, and a back-side band member different from the abdominal-side band member. The back-side band member has a central portion fixed to an other end part in the vertical direction of the absorbent main body, while covering the other end part from the non-skin side of the absorbent main body. The back-side band member has a length in the vertical direction longer than the abdominal-side band member. Each of the abdominal-side and back-side band members has an elastic member. The abdominal-side band member and the absorbent main body overlap at an overlap portion, the overlap portion including at least a part where the elastic member is disconnected.

10 Claims, 9 Drawing Sheets

(52) U.S. Cl.
CPC .... *A61F 13/84* (2013.01); *A61F 2013/49033* (2013.01); *A61F 2013/8497* (2013.01)

(58) Field of Classification Search
USPC .............. 604/385.24, 385.28, 385.29, 385.3
See application file for complete search history.

(56) References Cited

U.S. PATENT DOCUMENTS

| | | | |
|---|---|---|---|
| 2011/0071488 A1 | 3/2011 | Kuwano et al. | |
| 2013/0060219 A1* | 3/2013 | Mukai | A61F 13/49058 604/385.3 |

FOREIGN PATENT DOCUMENTS

| | | | |
|---|---|---|---|
| JP | 2005-237768 A | 9/2005 | |
| JP | 2009-528888 A | 8/2009 | |
| JP | 2009-240640 A | 10/2009 | |
| JP | 2010-188201 A | 9/2010 | |
| JP | 2013-183938 A | 9/2013 | |
| JP | 2013-255573 A | 12/2013 | |

OTHER PUBLICATIONS

Office Action in PH Application No. 1/2016/501802, dated Oct. 10, 2018, 4pp.
Written Opinion of the ISA in PCT/JP2015/051379, dated Apr. 21, 2015.
Office Action in JP Application No. 2014-066020, dated Dec. 12, 2017, 2pp.
Office Action in CN Application No. 201580016801.X, dated Jan. 28, 2019, 8pp.
Office Action in AU Application No. 2015235782, dated Feb. 22, 2019, 4pp.
Office Action in PH Application No. 1/2016/501802, dated Jun. 13, 2019, 3pp.
Office Action in CN Application No. 201580016801.X, dated Jul. 12, 2019, 6pp.

* cited by examiner

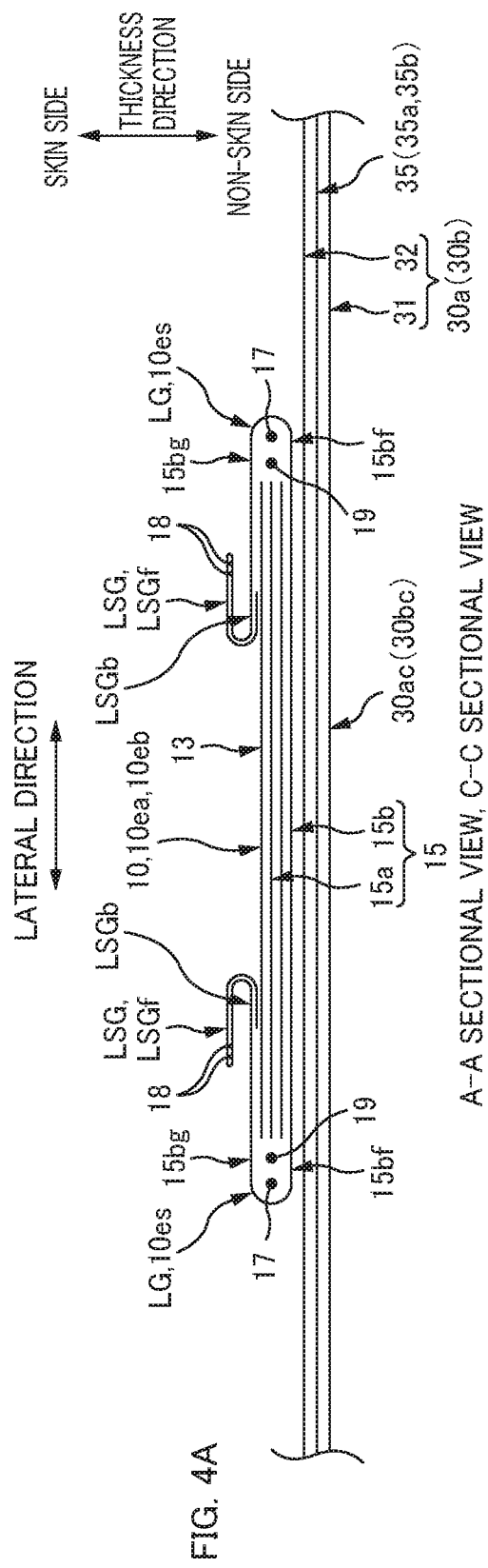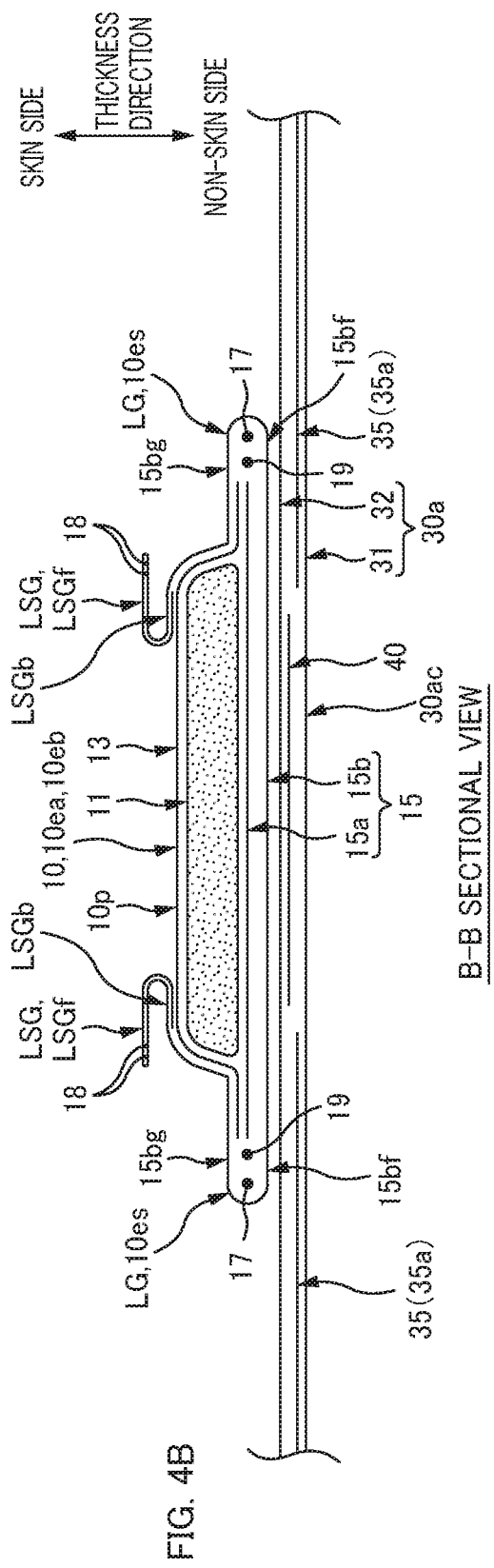

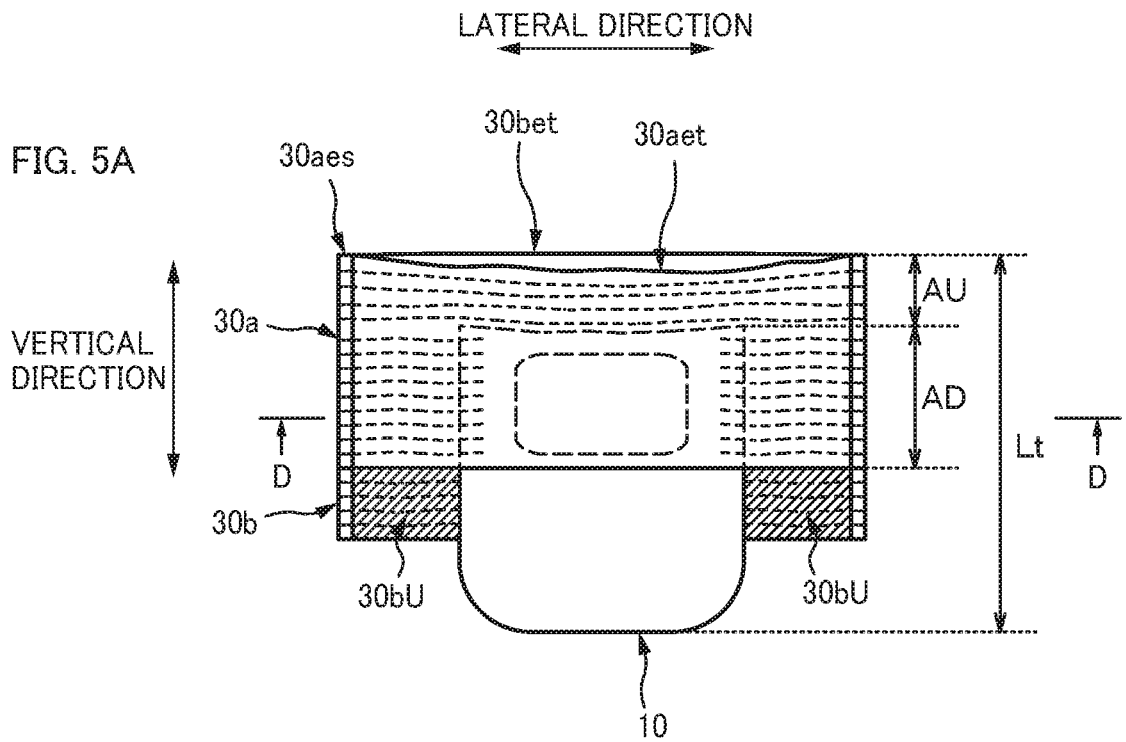
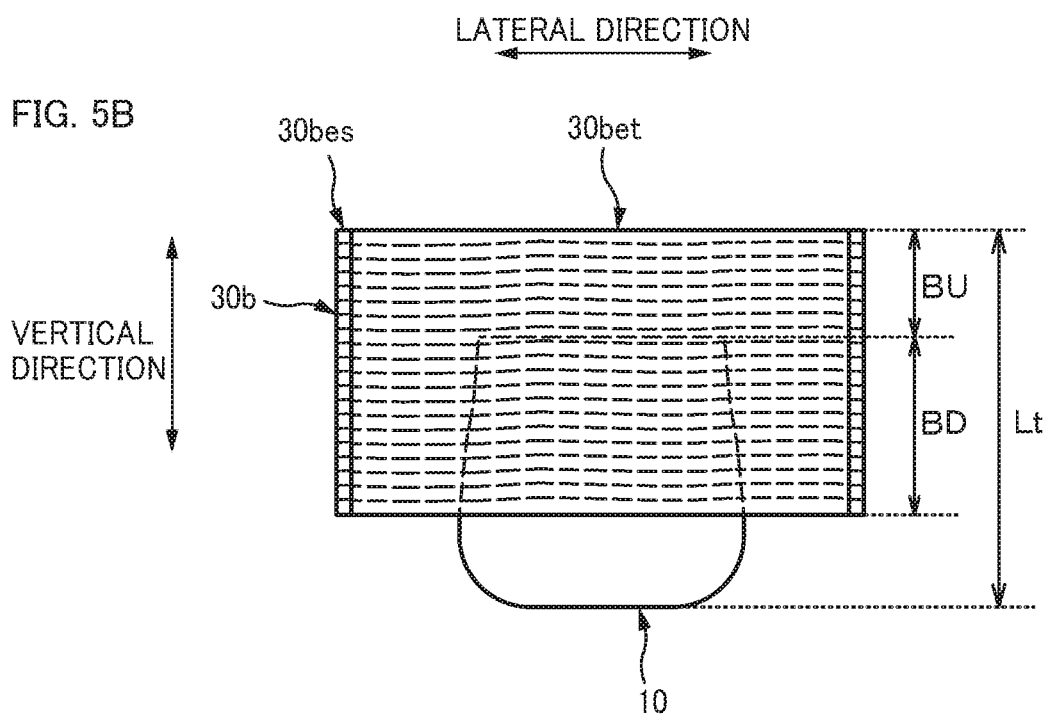

ABSORBENT ARTICLE

RELATED APPLICATIONS

The present application is a national phase of International Application Number PCT/JP2015/051379, filed Jan. 20, 2015, which claims priority to Japanese Application Number 2014-066020, filed Mar. 27, 2014.

TECHNICAL FIELD

The present disclosure relates to an absorbent article.

BACKGROUND ART

A pant-type disposable diaper is known as an absorbent article that absorbs exudates. Commonly, in a pant-type disposable diaper, a stretchable member such as a rubber thread is mounted to a waist part, to provide stretchability in the width direction, so that the diaper is less likely to deviate in position when worn. In such a case, in order to restrain the formation of inappropriate wrinkles and/or the excessive pressure on a wearer's torso part, which is caused by a stretchable member, the arrangement of such a stretchable member may be changed. For example, Patent Literature 1 discloses an example of a pant-type disposable diaper in which a non-stretchable region is provided in an abdominal-side central portion in a waist part, so that the formation of such wrinkles in this region is restrained as well as fittingness can be obtained when worn.

CITATION LIST

Patent Literature

[PTL 1] Japanese Patent Application Laid-open Publication No. 2002-272783

SUMMARY

Technical Problem

In such a disposable diaper, since a non-stretchable region is provided in an abdominal-side central portion in a waist part, a force to contract an absorbent body in a width direction does not act in this region. On the other hand, since a non-stretchable region is not provided in a back-side central portion of the waist part, a force to contract the absorbent body in the width direction acts in such a region. Accordingly, the absorbent body is configured to be larger in the width direction on the abdominal side than on the back side.

However, with such a configuration, judgment between front and back of a diaper (judgment between abdominal side and back side) may be difficult. In general, pants and the like have the surface area larger on the back side (buttock side) than on the abdominal side, and thus, pant-type disposable diapers are likely to be considered such that the side on which the absorbent body is larger in the width direction is the back side. Further, in such a disposable diaper, configurations are substantially the same between the abdominal side and the back side, except that the absorbent body is different in area in the width direction. Thus, judgment between front and back is difficult.

Embodiments according to the present disclosure have been provided in view of the above, and are directed to provision of a disposable diaper on which judgement between front and back can more easily be made.

Solution to Problem

In view of such an aspect, provided is an absorbent article having a vertical direction and a lateral direction intersecting the vertical direction, the absorbent article comprising:

an absorbent main body provided along the vertical direction, the absorbent main body being configured to absorb excreta;

an abdominal-side band member provided along the lateral direction, the abdominal-side band member having a central portion in the lateral direction fixed to one end part in the vertical direction of the absorbent main body, while covering the one end part from a non-skin side of the absorbent main body; and a back-side band member provided along the lateral direction as a member different from the abdominal-side band member, the back-side band member having a central portion in the lateral direction fixed to an other end part in the vertical direction of the absorbent main body, while covering the other end part from the non-skin side of the absorbent main body, the back-side band member having a length in the vertical direction longer than a length in the vertical direction of the abdominal-side band member, the abdominal-side band member and the back-side band member each having an elastic member disposed thereto along the lateral direction, the elastic member being configured to expand and contract along the lateral direction, the abdominal-side band member and the absorbent main body overlapping each other at an overlap portion, the overlap portion including at least a part where the elastic member is disconnected.

Other aspects will be made clear through the present specification with reference to the accompanying drawings.

Advantageous Effects

With embodiments according to the present disclosure, it is possible to provide a disposable diaper on which judgment between front and back is more easily made.

BRIEF DESCRIPTION OF DRAWINGS

FIG. 4A is a cross-sectional view taken on line A-A and the cross-sectional view taken on line C-C of FIG. 2, and FIG. 4B is a cross-sectional view taken on line B-B sectional view of FIG. 2.

FIG. 5A is a schematic diagram illustrating a diaper 1 formed into a pant shape when viewed from the front (abdominal side).

FIG. 5B is a schematic diagram illustrating a diaper 1 formed into a pant shape when viewed from the back (back side).

DESCRIPTION OF EMBODIMENTS

Figure 1:
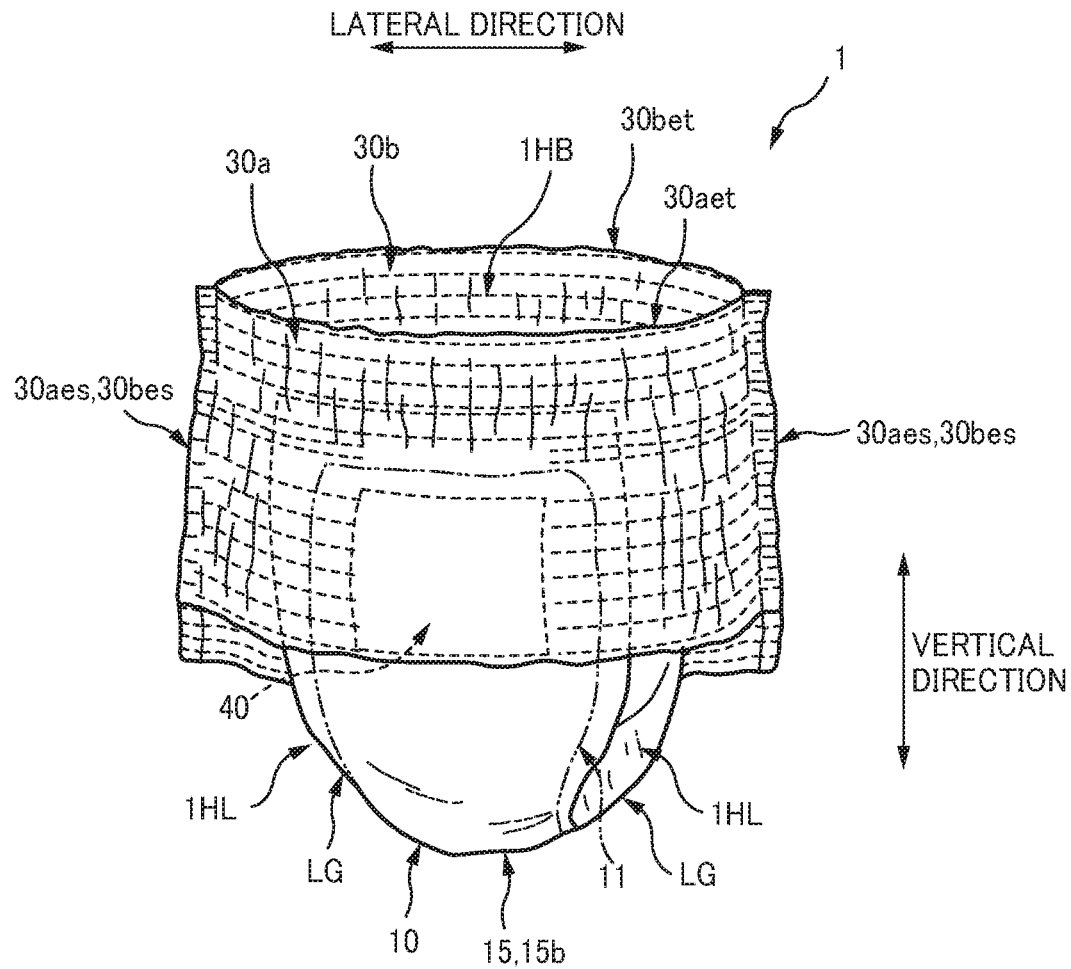
FIG. 1 is a schematic perspective view illustrating a three-piece type disposable diaper (diaper 1) according to an embodiment of the present disclosure.

At least the following matters will be made clear by the description in the present specification and the accompanying drawings.

An absorbent article having a vertical direction and a lateral direction intersecting the vertical direction, the absorbent article comprises: an absorbent main body provided along the vertical direction, the absorbent main body being configured to absorb excreta; an abdominal-side band member provided along the lateral direction, the abdominal-side band member having a central portion in the lateral direction fixed to one end part in the vertical direction of the absorbent main body, while covering the one end part from a non-skin side of the absorbent main body; and a back-side band member provided along the lateral direction as a member different from the abdominal-side band member, the back-side band member having a central portion in the lateral direction fixed to an other end part in the vertical direction of the absorbent main body, while covering the other end part from the non-skin side of the absorbent main body, the back-side band member having a length in the vertical direction longer than a length in the vertical direction of the abdominal-side band member, the abdominal-side band member and the back-side band member each having an elastic member disposed thereto along the lateral direction, the elastic member being configured to expand and contract along the lateral direction, the abdominal-side band member and the absorbent main body overlapping each other at an overlap portion, the overlap portion including at least a part where the elastic member is disconnected.

According to such an absorbent article, a clear external difference is presented between the front side and the back side. Thus, a user can more easily make a judgment between front and back.

In some embodiments of such an absorbent article, a length from an end on one side in the vertical direction of the absorbent main body to an upper end in the vertical direction of the abdominal-side band member is different from a length from an end on an other side in the vertical direction of the absorbent main body to an upper end in the vertical direction of the back-side band member.

According to such an absorbent article, a user feels different to the touch between when touching a front-side upper end part and when touching a back-side upper-end part, and thus front/back judgment on the absorbent article is more easily made not only by sight but also by touch.

In some embodiments of such an absorbent article, the absorbent main body includes an absorbent core, the absorbent core being formed such that a liquid absorbent material is stacked in a predetermined thickness, and an area where the absorbent core is not disposed, in a region overlapping with the absorbent main body, in the central portion in the lateral direction of the abdominal-side band member, the area including a part where the elastic member is disconnected, is provided between an area where the absorbent core is disposed, in the region overlapping with the absorbent main body, in the central portion in the lateral direction of the abdominal-side band member, the area including a part where the elastic member is disconnected, and an area not overlapping with the absorbent main body in the central portion in the lateral direction of the abdominal-side band member, in a region where the elastic member is disposed in a state stretched over between one end side and an other end side thereof in the lateral direction, so that, when the absorbent main body is two-folded at a central part thereof in the vertical direction and side-edge parts in the lateral direction of the abdominal-side band member are coupled to side-edge parts in the lateral direction of the back-side band member, respectively, the upper end in the vertical direction of the abdominal-side band member is different in position in the vertical direction from the upper end in the vertical direction of the back-side band member.

According to such an absorbent article, the upper edge of the back-side band member is different in position from the upper edge of the abdominal-side band member. When the absorbent article is viewed from the front, such upper edge parts of the abdominal-side band member and the back-side band member can be seen. However, when the absorbent article is viewed from the back, only the upper edge part of the back-side band member can be seen and the upper edge part of the abdominal-side band member can not be seen. Accordingly, front/back judgment can be made more precisely.

In some embodiments of such an absorbent article, a length in the vertical direction of the back-side band member is longer than a half of a length in the vertical direction of the absorbent article, when the absorbent main body is two-folded at the central part thereof in the vertical direction and the side-edge parts in the lateral direction of the abdominal-side band member are coupled to the side-edge parts in the lateral direction of the back-side band member, respectively.

According to such an absorbent article, when the absorbent article that is formed in a pant-shape is viewed from the back side, the back-side band member can be seen over a range equal to or more than a half thereof in the vertical direction. Thus, the difference in external shape as compared with the case when the absorbent article is viewed from the front becomes clearer. Accordingly, it becomes less likely to make a mistake in judging between the front and the back of the absorbent article.

In some embodiments of such an absorbent article, when the absorbent main body is two-folded at the central part thereof in the vertical direction and the side-edge parts in the lateral direction of the abdominal-side band member are coupled to the side-edge parts in the lateral direction of the back-side band member, respectively, a length between each end in the lateral direction of an overlap portion, overlapping with the back-side band member, in the absorbent main body and each of the side-edge parts in the lateral direction of the back-side band member is longer than a length between each end in the lateral direction of an overlap portion, overlapping with the abdominal-side band member, in the absorbent main body and each of the side-edge parts in the lateral direction of the abdominal-side band member.

According to such an absorbent article, the abdominal-side band member contracts in the lateral direction, thereby causing a surface thereof to be deformed. With such deformation of the surface rising up and down, wrinkles are formed. On the other hand, contraction in the lateral direction in the back-side band member is smaller than that in the abdominal-side band member. Thus, formed wrinkles are less noticeable. With such a difference in wrinkles, front/back judgment on the absorbent article can be facilitated.

In some embodiments of such an absorbent article, stress of the elastic member disposed between the each end in the lateral direction of the overlap portion, overlapping with the back-side band member, in the absorbent main body and each of the side-edge parts in the lateral direction of the back-side band member is greater than stress of the elastic member disposed between the each end in the lateral direction of the overlap portion, overlapping with the abdominal-side band member, in the absorbent main body and each of the side-edge parts in the lateral direction of the abdominal-side band member.

According to such an absorbent article, deformation becomes greater on the abdominal side, on which stress is smaller. Thus, large wrinkles are more likely to be formed on the abdominal side than on the back side. Accordingly, front/back judgment is facilitated.

In some embodiments of such an absorbent article, an area on an upper end in the vertical direction of the absorbent main body has a color different from a color of an area other than the area on the upper end.

According to such an absorbent article, a colored line can be seen along the upper end of the absorbent main body. Thus, it is more easily recognized that the side on which the line is visible is the front side (abdominal side) of the absorbent article.

In some embodiments of such an absorbent article, when the absorbent main body is two-folded at the central part thereof in the vertical direction and the side-edge parts in the lateral direction of the abdominal-side band member are coupled to the side-edge parts in the lateral direction of the back-side band member, respectively, at least a part of the elastic member disposed to a portion, not overlapping with the abdominal-side band member, of the back-side band member, in the elastic member disposed to the back-side band member, has a color different from a color of the elastic member disposed to the abdominal-side band member.

According to such an absorbent article, the elastic member disposed to the back-side band member is seen differently between when viewed from the front and when viewed from the back. Accordingly the front and the back can be judged more clearly on the absorbent article.

===Embodiment===

<Configuration of Disposable Diaper>

Figure 2:
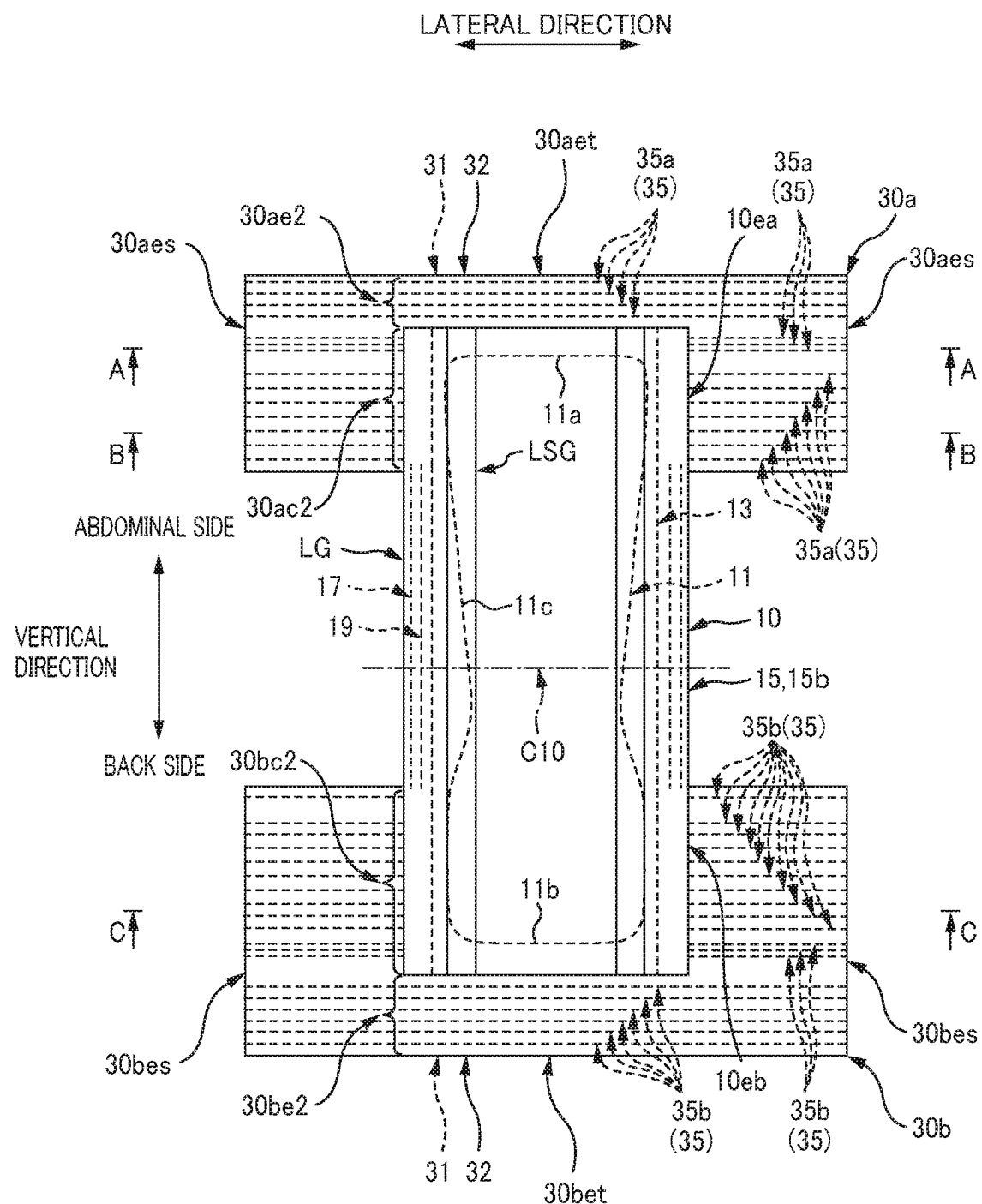
FIG. 2 is a schematic plan view illustrating a diaper 1 in its unfolded state when viewed from a skin side.
Figure 3:
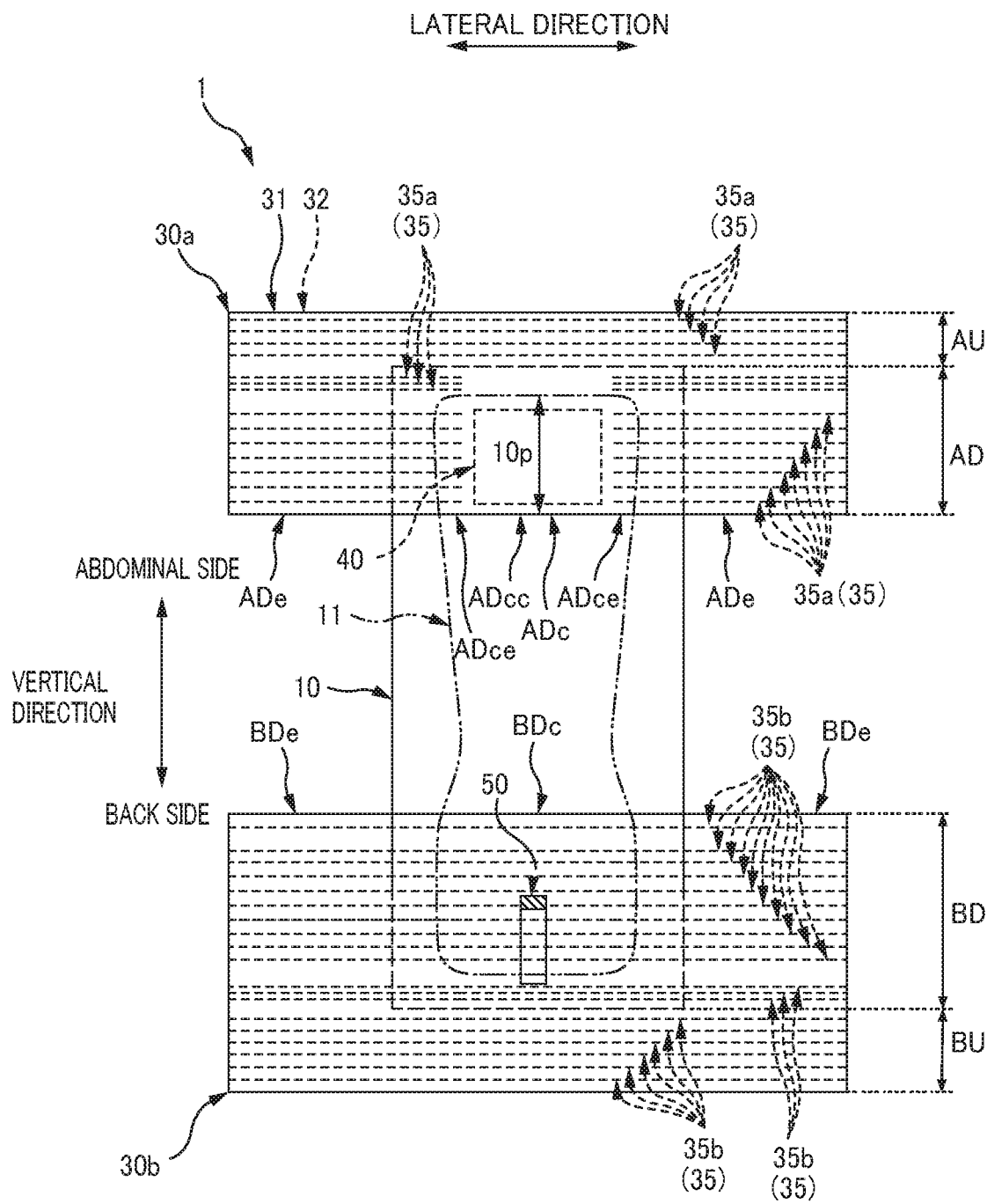
FIG. 3 is a schematic plan view illustrating a diaper 1 when seen from a non-skin side.

FIG. 1 is a schematic perspective view illustrating a disposable diaper (diaper 1) as an example of an absorbent article according to an embodiment of the present disclosure. FIG. 2 is a schematic plan view illustrating the diaper 1 in its unfolded state when viewed from a skin side. FIG. 3 is a schematic plan view illustrating the diaper 1 when seen from a non-skin side. FIG. 4A is a cross-sectional view taken on line A-A and also the cross-sectional view taken on line C-C of FIG. 2, and FIG. 4B is a cross-sectional view taken on line B-B of FIG. 2.

As illustrated in FIGS. 2, 4A, and 4B, the diaper 1 has a vertical direction, a lateral direction, and a thickness direction, as three directions orthogonal to one another. Further, the diaper 1 is of a so-called three-piece type, and includes three components 10, 30a, and 30b. That is, the diaper 1 includes: an absorbent main body 10 configured to be provided to a crotch of a wearer and absorb excreta such as urine, as a first component; an abdominal-side band member 30a configured to cover structured to cover an abdomen side of the wearer, as a second component; and a back-side band member 30b configured to cover a back side of the wearer, as a third component. In the unfolded state in FIG. 2, while the abdominal-side band member 30a (upper side in the vertical direction in FIG. 2) and the back-side band member 30b (lower side in the vertical direction in FIG. 2) are arranged in parallel to each other with a space t herebetween in the vertical direction, the absorbent main body 10 bridges the space therebetween. Then, end parts 10ea, 10eb in the lateral direction of the absorbent main body 10 are joined and fixed to the closest band members 30a, 30b, respectively, resulting in the external appearance thereof being formed in a substantially H-shape in plan view. From this state, the absorbent main body 10 is folded into two at its substantially central part 10C in the longitudinal direction as a folding position. When the abdominal-side band member 30a and the back-side band member 30b, opposed to each other in this two-folded state, are joined/coupled at abdominal-side band-member side-edge parts 30aes and back-side band-member side-edge parts 30bes (i.e., end parts in the lateral direction), respectively, which are the parts to come in contacted with a wearer's sides, these band members 30a, 30b are formed in an annular shape. Thereby, the diaper 1 when worn is configured, in which a waist opening 1HB and a pair of leg openings 1HL are formed as illustrated in FIG. 1. Further, in the following description, an end part in the vertical direction of the abdominal-side band member 30a, which forms an annular opening of the opening 1HB, is referred to as an abdominal-side band-member upper-edge part 30aet, and an end part in the vertical direction of the back-side band member 30b, which forms an annular opening of the opening 1HB, is referred to as a back-side band-member upper-edge part 30bet.

Various coupling configurations can be employed as a coupling configuration in which the abdominal-side band-member side-edge parts 30aes are coupled to the back-side band-member side-edge parts 30bes, respectively. Then, for example, with a coupling configuration that is not detachably configured by welding, etc., a pant-type diaper can be configured, and with a coupling configuration that is detachably configured using a fastening tape member (not shown), etc., an open-type diaper can be configured. In this example, the former coupling configuration is employed, and thus the diaper 1 according to an embodiment of the present disclosure is of a pant-type.

Further, in the following description, the vertical direction, the lateral direction, and the thickness direction of the diaper 1 is simply referred to as "the vertical direction", "the lateral direction", and "the thickness direction", respectively. Note that, with respect to the thickness direction, the side to come in contact with a wearer is referred to as the "skin side", the side opposite thereto is referred to as the "non-skin side". Further, since "the lateral direction" of the diaper 1 can also be a "width direction" of the absorbent main body 10 when the diaper is formed in FIG. 1, the "lateral direction" may be referred to as the "width direction" in the following description.

Hereinafter, the three components 10, 30a, and 30b configuring the diaper 1 will be described with reference to FIGS. 1 to 4B.

As illustrated in FIGS. 2 and 4B, the absorbent main body 10 comprises: an absorbent core 11, a surface sheet member 13 that covers the absorbent core 11 from the skin side of the core 11; and a rear-surface sheet member 15 that covers the absorbent core 11 from the non-skin side of the core 11 to configure an exterior of the absorbent main body 10.

The absorbent core 11 is a member formed such that a liquid absorbent material is stacked, and capable of absorbing exudates such as urine. For example, liquid absorbent fiber such as pulp fiber can be used as the liquid absorbent material. Note that the absorbent core 11 may contain, for example, superabsorbent polymer as a liquid-absorbent particle, or may contain a liquid absorbent material other than liquid absorbent fiber and a liquid-absorbent particle. Further, the absorbent core 11 may be covered with a liquid-permeable sheet (not shown) such as tissue paper.

The absorbent core 11 according to an embodiment of the present disclosure comprises: an abdominal-side end part 11a, which is an upper end part in the vertical direction in FIG. 2; and a back-side end part 11b, which is a lower end part in the vertical direction in FIG. 2. The absorbent core 11 also includes a constriction part 11c, which is provided between the abdominal-side end part 11a and the back-side end part 11b, and has a width in the lateral direction smaller than those of the abdominal-side end part 11a and the back-side end part 11b. Accordingly, the absorbent core 11 is configured to be formed in a substantially hourglass shape in plan view as illustrated in FIG. 2.

The surface sheet member 13 is a sheet-like member that covers the absorbent core 11 from the skin side, and is, for example, a liquid permeable nonwoven fabric having a planer size larger than the absorbent core 11 (see FIG. 4B). Further, the rear-surface sheet member 15 is a sheet-like member that covers the absorbent core 11 from the non-skin side, and is a sheet having a planer size larger than that of the absorbent core 11, and is, for example, a sheet having a double-layer structure in which a liquid-impermeable leak-proof sheet 15a, such as polyethylene or polypropylene, and an exterior sheet 15b, such as a nonwoven fabric, are bonded to each other. Then, the leak-proof sheet 15a of the rear-surface sheet member 15 and the surface sheet member 13 are bonded to each other in a frame manner at a portion extending outside from the four sides of the absorbent core 11, with the absorbent core 11 being sandwiched between the rear-surface sheet member 15 and the surface sheet member 13, thereby substantially forming the absorbent main body 10.

Further, in the diaper 1, as illustrated in FIGS. 1, 2, and 4B, so-called leg side-gathers (barrier cuffs) LSG and leg gathers LG are formed with the exterior sheet 15b. The leg side-gathers LSG are leakage-proof wall parts provided to stand at the end parts in the lateral direction of the surface sheet member 13, respectively, while the leg gathers LG are elastic parts around legs that are formed to the leg openings 1HL, 1HL, respectively. Such exterior sheet 15b will be described in details. First, as illustrated in FIG. 4B, the size in the lateral direction of the exterior sheet 15b is made sufficiently larger than that of the leak-proof sheet 15a. That is, the exterior sheet 15b greatly extends outside in the lateral direction with respect to both sides in the lateral direction of the leak-proof sheet 15a. Such extending portions 15bf each are folded back toward the central side in the lateral direction at a position forming an end part 10es in the lateral direction of the absorbent main body 10, which serves as a folding portion. Then, a leg elastic member 17 and a leg auxiliary elastic member 19, such as rubber threads, are fixed along the vertical direction near the folding portion, in a state stretched in the vertical direction, thereby forming the above described leg gathers LG.

Note that, in FIG. 2, the leg elastic member 17 and the leg auxiliary elastic member 19 are arranged so as not to intersect each of an abdominal-side band elastic member 35a and a back-side band elastic member 35b. In this case, the stretchability (elasticity) in the leg elastic member 17 and the leg auxiliary elastic member 19 and the stretchability (elasticity) in the abdominal-side band elastic member 35a and the back-side band elastic member 35b do not affect each other. That is, even though the abdominal-side band elastic member 35a and/or the back-side band elastic member 35b contract inward in the lateral direction (width direction), the leg elastic member 17 and the leg auxiliary elastic member 19 are less affected by the force in the lateral direction (width direction). Thereby, the leg gathers LG become less likely to be deformed, which can facilitate functioning as leakage-proof wall parts. Whereas, the leg elastic member 17 and the leg auxiliary elastic member 19 may be arranged so as to intersect each of the abdominal-side band elastic member 35a and the back-side band elastic member 35b (not shown). In this case, the stretchability in the leg elastic member 17 and the leg auxiliary elastic member 19 and the stretchability in the abdominal-side band elastic member 35a and the back-side band elastic member 35b affect each other. When a wearer wearing the diaper 1 excretes, the absorbent main body 10 having absorbed excreta becomes heavy in weight, which lowers the absorbent main body 10 downward. Accordingly, the leg elastic member 17 and the leg auxiliary elastic member 19 become likely to stretch downward. As a result, a space increases between the wearer's legs and the leg openings 1HL, which may cause excreta to leak out from the space. However, the leg elastic member 17 and the leg auxiliary elastic member 19 are arranged to intersect the abdominal-side band elastic member 35a and the back-side band elastic member 35b, thereby being able to restrain the leg elastic member 17, etc., from stretching downward by the abdominal-side band elastic member 35a, etc. Accordingly, even when a wearer excretes in the absorbent main body 10, the absorbent main body 10 is less lowered downward, which restrains excreta from leaking outside from a space between the wearer's legs and the leg openings 1HL, or other problems from occurring.

Note that the leg auxiliary elastic member 19 is not necessarily provided, but only the leg elastic member 17 may form the leg gathers LG. Further, a folded portion 15bg extends further toward the center in the lateral direction, and is joined to an end part in the lateral direction of the surface sheet member 13 at such a position as to cover the end part. Then, a part joined with the end part acts as the base end part LSGb of the leg side-gathers LSG. That is, a part on the further end side in the lateral direction with respect to the base end part LSGb is configured to be able to stand from the surface sheet member 13 as a free end part LSGf. Further, LSG elastic member(s) 18 such as a rubber thread is (are) fixed along the vertical direction to the end part of the free end part LSGf along the vertical direction, in a state stretched in the vertical direction. Thus, with the contraction in the vertical direction of the LSG elastic member 18, the absorbent main body 10 is curved in the vertical direction such that the surface sheet member 13 is positioned on the inner circumferential side. During such a curved condition, with the contractile force being exerted by the LSG elastic member 18, the free end part LSGf contracts in the vertical direction to rise from the surface sheet member 13, which causes the free end part LSGf to function as the leg side-gathers (barrier cuffs) LSG.

Note that, although not shown, a liquid-permeable sheet such as tissue paper may be placed as a second sheet between the surface sheet member 13 and the absorbent core 11, or between the rear-surface sheet member 15 and the absorbent core 11, according to the circumstances.

As illustrated in FIG. 2, the abdominal-side band member 30a and the back-side band member 30b each are, for example, a sheet member each made of a soft sheet, such as a nonwoven fabric, having a substantially rectangular shape in plan view. Here, as illustrated in FIGS. 4A and 4B, the nonwoven fabrics 31, 32 are joined in a two-layer manner, to form each of the abdominal-side band member 30a and the back-side band member 30b. The abdominal-side band member 30a and the back-side band member 30b respectively have central portions 30ac, 30bc in the lateral direction overlapping with and joined to the end parts 10*ea*, 10*eb* in the vertical direction of the absorbent main body 10, respectively, at the central portions 30*ac*, 30*bc* of the band members 30*a*, 30*b*, while covering the end parts 10*ea*, 10*eb* in the vertical direction of the absorbent main body 10 from the non-skin side of the absorbent main body 10, respectively. Note that the two nonwoven fabrics 31, 32 may not be of the same size.

The absorbent main body 10 overlaps with the central portion 30*ac* of the abdominal-side band member 30*a* and the central portion 30*bc* of the back-side band member 30*b*, in such a manner as not to overlap with an end part 30*ae*2 in the vertical direction of the abdominal-side band member 30*a* and an end part 30*be*2 in the vertical direction of the back-side band member 30*b*, but to overlap with parts 30*ac*2, 30*bc*2, which are positioned more central in the vertical direction than the end parts 30*ae*2, 30*be*2 (see FIG. 2). Accordingly, the end parts 30*ae*2, 30*be*2 in the vertical direction of the abdominal-side band member 30*a* and the back-side band member 30*b* result in the parts 30*ae*2, 30*be*2, in which the absorbent main body 10 does not overlap in a band like manner over the entire length in the lateral direction. Note that such not-overlapping parts 30*ae*2, 30*be*2 are parts configure the waist opening 1HB of the diaper 1 (FIG. 1). Thus, the elastic member 35, which will be described later, is provided to the parts 30*ae*2, 30*be*2 in a continual manner over the substantially entire length in the lateral direction of the parts 30*ae*2, 30*be*2.

As illustrated in FIGS. 2, 4A, and 4B, the elastic members 35, 35 . . . , such as rubber threads, etc., are joined and fixed to the nonwoven fabrics 31, 32, in a state inserted along the lateral direction between the two nonwoven fabrics 31, 32 with respect to the band members 30*a*, 30*b* and stretched in the lateral direction. Accordingly, the stretchability (elasticity) in the lateral direction is provided to each of the abdominal-side band member 30*a* and the back-side band member 30*b*. Further, such a plurality of elastic members 35, 35 . . . are provided in such a manner as to be arranged side by side in the vertical direction with a space provided each therebetween in the vertical direction. In a specification, the elastic member 35 provided to the abdominal-side band member 30*a* is referred to as the abdominal-side band elastic member 35*a*, and the elastic member 35 provided to the back-side band member 30*b* is referred to as the back-side band elastic member 35*b*.

Hereinafter, for convenience sake, as illustrated in FIG. 3, the abdominal-side band member 30*a* is divided in the vertical direction into two regions AU, AD, and such two regions AU, AD arranged side by side in the vertical direction are referred to as the "upper region AU" and the "lower region AD" from the end side to the central side in the vertical direction. Similarly, the back-side band member 30*b* is divided in the vertical direction into two regions BU, BD, and such regions are referred to as the "upper region BU" and the "lower region BD" from the end side to the central side in the vertical direction. Note that, as understood from FIG. 3, all the regions AU, AD, BU, and BD are band-like regions along the lateral direction.

The upper region AU in the abdominal-side band member 30*a* is a part configuring the waist opening 1HB of the diaper 1. Further, the region AU is a region in which the absorbent main body 10 does not overlap over the entire length in the lateral direction. And, in this upper region AU, the abdominal-side band elastic member 35*a* is fixed in a state stretched in the lateral direction while being continually arranged substantially throughout the length from one end part to the other end part in the lateral direction in the region AU. Thus, the stretchability in the lateral direction over the substantially entire length in the lateral direction is provided to the upper region AU based on the abdominal-side band elastic member 35*a*, and this stretchability results in the stretchability of the waist opening 1HB in the diaper 1. Similarly, the upper region BU in the band member 30*b* configures the waist opening 1HB of the diaper 1. And, in the region BU, the back-side band elastic member 35*b* is fixed in a state stretched in the lateral direction while being continually arranged substantially throughout the length from one end part to the other end part in the lateral direction in the region BU.

A portion 10*p*, where the absorbent core 11 exists, of the absorbent main body 10 overlaps with and is fixed to the central portion ADc in the lateral direction in the lower region AD of the abdominal-side band member 30*a*. Note that the absorbent main body 10 does not overlap with parts ADe, ADe, which are located on both the sides of the aforementioned central portion ADc in the lower region AD.

Further, the elastic member 35 is fixed in each of the parts ADe, ADe, in a state stretched in the lateral direction while being arranged to continue over the substantially entire length between one end part and the other end part in the lateral direction in the part ADe. Accordingly, the stretchability in the lateral direction is provided to the parts ADe, ADe substantially throughout the length in the lateral direction.

On the other hand, in the aforementioned central portion ADc, the elastic member 35 is arranged in a manner not connected in the lateral direction. Specifically, in this example, end parts of the aforementioned elastic member 35 are located in end parts ADce, ADce on both sides in the lateral direction in the central portion ADc. And, a central part ADcc in the lateral direction in the aforementioned central portion ADc includes at least one part in which the elastic member 35 is disconnected. Thus, in the aforementioned central portion ADc, the elastic member 35 is arranged in the lateral direction in a disconnected manner. Then, in the case where the elastic member 35 is disconnected in the central part ADcc in the central portion ADc as such, stretchability is substantially not provided to the central part ADcc, thereby restraining the central part ADcc from contracting in the lateral direction. Accordingly, the contraction in the lateral direction (width direction) of the absorbent core 11 is restrained, thereby restraining the absorbent core 11 from becoming wrinkled, so that the skin side surface of the absorbent core 11 is maintained substantially flat. As a result, it becomes possible to effectively restrain liquid absorption in the absorbent core 11 from being disturbed, and also restrain excreta from leaking, which is caused by formation of such wrinkles.

Meanwhile, the back-side band elastic member 35*b* is fixed, in a state stretched in the lateral direction, in a central portion BDc in the lateral direction and parts BDe, BDe located on both sides of the central portion ADc in the lower region BD of the back-side band member 30*b*, while being arranged to continue over the substantially entire length between one end part to the other end part in the lateral direction. That is, stretchability in the lateral direction is provided substantially throughout the length in the lateral direction, including the absorbent core 11, in the lower region BD. Accordingly, in this region, the absorbent core 11 contracts in the lateral direction (width direction), however, on the back side, "feces" whose excretion range is narrower than that of "urine" are mainly excreted. Excreta are less likely to leak from the absorbent core 11.

Further, as illustrated in FIG. 3, an illustration sheet 40, in which illustration not shown such as an animal, etc., is formed, may be provided in the aforementioned central portion ADc of the lower region AD in the abdominal-side band member 30a. This illustration sheet 40 is also restrained from becoming wrinkled for the reason similar to the above. Further, the illustration sheet 40 may not be provided as a separate member, but, for example, such illustration may be printed directly onto the non-skin side surface of a corresponding area (i.e., near the central portion ADc in the lateral direction) in the absorbent main body 10 (exterior sheet 15b). In this case as well, wrinkles are restrained from being formed in an area near the central portion ADc in the lateral direction. Thus, with a configuration according to an embodiment of the present disclosure, such illustration can be seen more easily.

Further, as illustrated in FIG. 3, an aftertreatment tape 50 may be provided on the non-skin side surface of the back-side band member 30b. The aftertreatment tape 50 is a long and narrow tape-like member having an adhesive face, and is fixed to the back-side band member 30b in such a state as to be folded with the adhesive face positioned inside. When disposing of the used diaper 1, the folded aftertreatment tape 50 is extended to wind around the diaper 1 that is rolled up in the vertical direction, with the adhesive face facing to the diaper, thereby being able to hold the diaper 1 in a rolled up state. As a result, it is made possible to dispose of the diaper 1 without leaking excreta and the lik adhering inside (absorbent main body 10) the diaper 1. Furthermore, the aftertreatment tape 50 is not provided on the abdominal side (front side), whereas the aftertreatment tape 50 is provided on the back side (back side). This emphasizes the external difference between the front and the back of the diaper 1, thereby further facilitates front/back judgment.

<Configurations of Abdominal-side Band Member 30a and Back-side Band Member 30b>

In the diaper 1 according to an embodiment of the present disclosure, the length in the vertical direction of the back-side band member 30b (the length of the back-side band-member side-edge part 30bes, which is also expressed by the length in the vertical direction of BU+BD in FIG. 3) is longer than the length in the vertical direction of the abdominal-side band member 30a (the length of the abdominal-side band-member side-edge part 30aes, which is also expressed by the length in the vertical direction of AU+AD in FIG. 3). That is, the length in the vertical direction of the side-edge part 30bes in the back-side band member 30b is longer than the length in the vertical direction of the side-edge part 30aes in the abdominal-side band member 30a. As a result, when the abdominal-side band-member side-edge parts 30aes are coupled to the back-side band-member side-edge parts 30bes, respectively, to form the diaper 1 in a pant shape, an area of an end part in the vertical direction of the back-side band member 30b extends outside with respect to the abdominal-side band member 30a. Hereinafter, a description is made with reference to drawings.

FIG. 5A is a schematic diagram illustrating the diaper 1 formed in a pant shape when viewed from the front (abdominal side). FIG. 5B is a schematic diagram illustrating the diaper 1 formed in a pant shape when viewed from the back (back side).

In FIG. 5A, when the diaper 1 is viewed from the front (abdominal side), the back-side band member 30b has a portion that appears to extend, on the back side, from the abdominal-side band member 30a. In the case of this FIG. 5A, the areas 30bu, 30bu, which are illustrated by shaded areas on the lower side in the vertical direction in the back-side band member 30b, appear to extend greatly outside. Note that, when a wearer is wearing the diaper 1, such extending areas 30bu function as "buttock cover" configured to cover buttocks of the wearer. Further, in an region where the central portion ADc in the lateral direction of the abdominal-side band member 30a and the absorbent main body 10 (absorbent core 11) overlap each other, since the abdominal-side band elastic member 35a is cut to be disconnected, the abdominal-side band member 30a is less likely to contract in the width direction (lateral direction) in these area. Thus, the absorbent core 11 is less likely to become wrinkled, and also in a case where the aforementioned illustration sheet 40 is provided, the illustration depicted in the illustration sheet 40 is clearly viewable, thereby facilitating the judgment that the relevant area is on the front side of the diaper 1.

Meanwhile, in FIG. 5B, when the diaper 1 is viewed from the back (back side), the abdominal-side band member 30a is hidden by the back-side band member 30b, thereby not being viewable. Further, the back-side band elastic member 35b is provided substantially throughout the length in the lateral direction of the back-side band member 30b, and the back-side band elastic member 35b contracts, thereby wrinkling the absorbent main body 10 (absorbent core 11), which facilitates such a judgment that the diaper 1 is on the back side.

As such, in the diaper 1 according to an embodiment of the present disclosure, the length in the vertical direction of the back-side band member 30b is made longer than the length in the vertical direction of the abdominal-side band member 30a (BU+BD>AU+AD), as well as an overlap portion, where the abdominal-side band member 30a and the absorbent main body 10 overlap each other, includes a part where the abdominal-side band elastic member 35a is disconnected. Accordingly, when the diaper 1 is formed in a pant shape, a noticeable external difference between the front and the back (the abdominal side and the back side) appears. This enables a user to judge between the front and the back of the diaper 1 at a glance, and to be less likely to make a mistake in such a front/back judgment.

Note that, in one or more embodiments, the length in the vertical direction of the back-side band member 30b is longer than a half of the length (indicated by Lt in FIGS. 5A and 5B) in the vertical direction of the entire diaper 1 when the diaper 1 is formed in a pant form. In other words, in one or more embodiments, the length in the vertical direction of the back-side band member 30b is longer than a half of the length in the vertical direction of the diaper 1 when the absorbent main body 10 is two-folded at the central part in the longitudinal direction thereof and the side-edge parts 30aes of the abdominal-side band member 30a are coupled to the side-edge parts 30bes of the back-side band member 30b. With such a configuration, when the diaper 1 formed in a pant shape is viewed from the back (back side), the back-side band member 30b becomes viewable over the range more than a half in the vertical direction (see FIG. 5B). Accordingly, the difference in external shape between the diaper 1 when viewed from the front and the diaper 1 when viewed from the back becomes more outstanding. Thus, the front/back judgment on the diaper 1 can be made more precisely.

Further, in the central portion ADC in the lateral direction of the abdominal-side band member 30a, the stretchability in the lateral direction (width direction) of the upper region AU in the vertical direction is provided by virtue of the abdominal-side band elastic member 35a. Thus, in this region, the nonwoven fabrics 31, 32 configuring the abdominal-side band member 30*a* greatly contract in the width direction. Accordingly, when the diaper 1 is formed in a pant shape, the diaper contracts in the direction in which the diameter of the annular waist opening 1HB is reduced, that is, inwardly of the waist opening 1HB (toward the skin side of a wearer).

Meanwhile, in the central portion ADC in the lateral direction of the abdominal-side band member 30*a*, the abdominal-side band elastic member 35*a* includes a disconnected part in the lower region AD in the vertical direction. Thus, in this area, the stretchability in the lateral direction (width direction) is not provided, or is very small if provided (see FIG. 3). Here, in an overlap portion (referred to as ADd in FIG. 5A) overlapping with the absorbent core 11 in the lower region AD, the stiffness is increased due to the thickness in the absorbent core 11 itself (see FIG. 4B). Thus, even if the abdominal-side band member 30*a* contracts in the width direction in the aforementioned upper region AU, the overlap portion is less affected by such contraction. On the other hand, a portion (referred to as ADu in FIG. 5A) not overlapping with the absorbent core 11 in the lower region AD in the vertical direction is smaller in thickness (see FIG. 4A) and stiffness, due to not including the absorbent core 11. Thus, when the abdominal-side band member 30*a* contracts in the width direction, the portion ADu is more easily affected by such contraction. Therefore, when the diaper 1 is formed in a pant shape, the portion ADu in the abdominal-side band member 30*a* is affected by such contraction in the width direction in the upper region AU, thereby being pulled inwardly of the opening 1HB. On the other hand, the portion ADd in the abdominal-side band member 30*a* is not affected by such contraction in the width direction in the upper region AU, thereby not being pulled inwardly of the opening 1HB.

Then, the length in the vertical direction of the abdominal-side band member 30*a* is reduced by an amount corresponding to an amount by which the portion ADu in the abdominal-side band member 30*a* is pulled inwardly of the waist opening 1HB. As a result, the upper-edge part 30*aet* of the abdominal-side band member 30*a* is positioned lower than the upper-edge part 30*bet* of the back-side band member 30*b*. That is, when the diaper 1 is viewed from the front, the upper-edge part 30*aet* of the front-side band member 30*a* and the upper-edge part 30*bet* of the back-side band member 30*b* can be seen (see FIG. 5A). Whereas, when the diaper 1 is viewed from the back, the upper-edge part 30*aet* of the front-side band member 30*a* can not be seen (see FIG. 5B).

As such, in an embodiment of the present disclosure, when the diaper 1 is viewed from the front, the upper-edge part 30*aet* of the front-side band member 30*a* and the upper-edge part 30*aet* of the abdominal-side band member 30*a* can be seen, in addition to the extending area 30*bu* being viewable, which facilitates the front/back judgment on the diaper 1.

Figure 6:
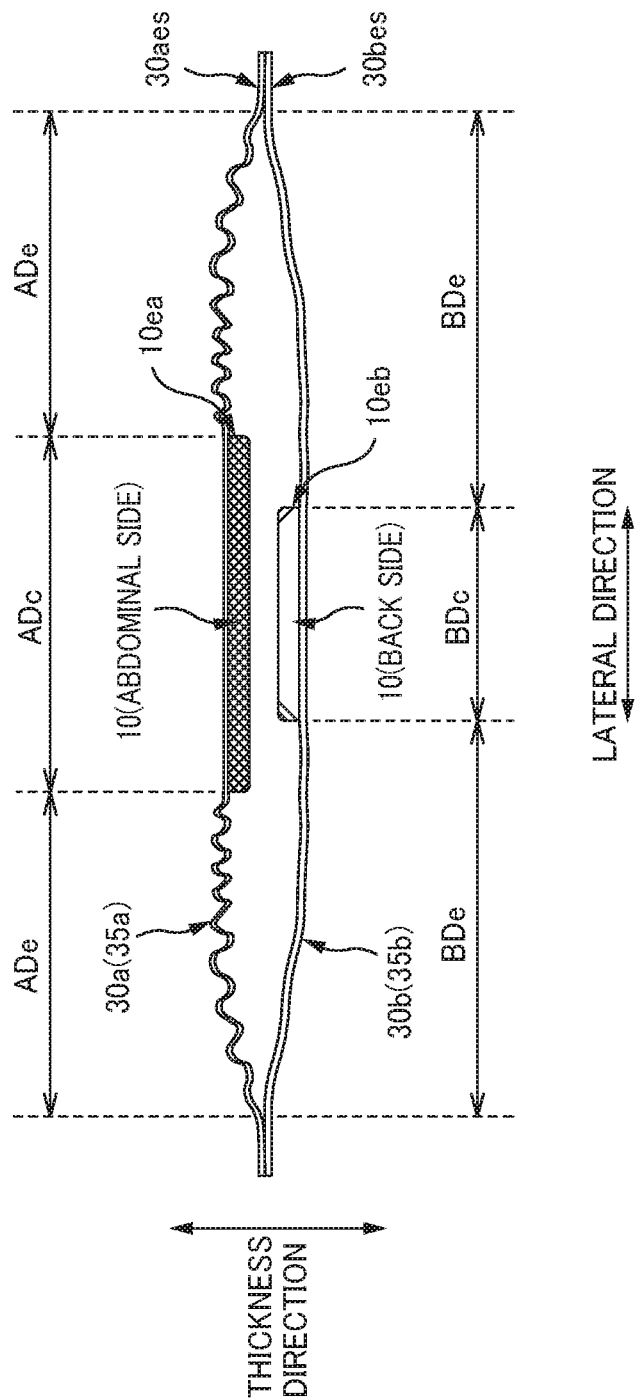
FIG. 6 is a diagram illustrating a cross-section taken on line D-D of FIG. 5A.

Next, wrinkles formed in the surfaces of the abdominal-side band member 30*a* and the back-side band member 30*b* will be focused. FIG. 6 is a diagram illustrating a cross-section taken on line D-D of FIG. 5A.

In a case where the diaper 1 is formed in a shape of a diaper illustrated in FIGS. 5A and 5B, the stretchability is acted by virtue of the back-side band elastic member 35*b* with respect to the back side, thereby causing the absorbent main body 10 to contract in the lateral direction (width direction). On the other hand, with respect to the abdominal side, the abdominal-side band elastic member 35*a* includes a disconnected part in the central portion ADc in the lateral direction, and thus stretchability is less likely to act. Accordingly, the absorbent main body 10 does not contract in the lateral direction (width direction). As a result, as illustrated in FIG. 6, the length in the lateral direction of the absorbent main body 10 is different between the abdominal side and the back side, in the central portion ADc (BDc) in the lateral direction.

Meanwhile, the length in the lateral direction of the entire abdominal-side band member 30*a* is to be equal to the length in the lateral direction of the entire back-side band member 30*b* under ordinary circumstances. Thus, when the abdominal-side band member 30*a* and the back-side band member 30*b* are coupled to each other at the side-edge parts 30*aes* and 30*bes*, respectively, both the end parts ADe in the lateral direction of the abdominal-side band member 30*a* contract by an amount corresponding to an amount by which the central portion BDc in the lateral direction of the back-side band member 30*b* contracts. That is, the length between each end (part) 10*eb* in the lateral direction of the absorbent main body 10 in an overlap portion where the absorbent main body 10 and the back-side band member 30*b* overlap each other and each of the side-edge parts 30*bes* in the lateral direction of the back-side band member 30*b*, results in being longer than the length between each end (part) 10*ea* in the lateral direction of the absorbent main body 10 in an overlap portion where the absorbent main body 10 and the abdominal-side band member 30*a* overlap each other and each of the side-edge parts 30*aes* in the lateral direction of the abdominal-side band member 30*a*.

Both the end parts ADe in the lateral direction of the abdominal-side band member 30*a* are configured with non-woven fabrics 31 and 32 having high flexibility, and contract in the lateral direction, thereby causing the surfaces of the nonwoven fabrics to be deformed. Such deformation of the nonwoven fabrics rises up and down in the thickness direction in FIG. 6, thereby forming wrinkles. On the other hand, wrinkles are formed also in the surface of the back-side band member 30*b*, however, a contract amount in both the end parts BDe in the lateral direction is smaller than that in the abdominal-side band member 30*a*. Thus, the amount and shapes of the formed wrinkles are less likely to be noticeable as compared with those in the abdominal-side band member 30*a*. That is, in the diaper 1, the sizes and shapes of the wrinkles formed in the surfaces of the abdominal-side band member 30*a* and the back-side band member 30*b* are different from each other, and the wrinkles are noticeable on the front side whereas the wrinkles are less noticeable on the back side. Such differences in the wrinkles can facilitate the front/back judgment on the diaper 1. Further, since deformation is less likely to occur and the wrinkles are less noticeable on the back side, the "buttock cover" can easily be recognized when the diaper 1 is seen, resulting in less mistakes in judgment between front and back.

Further, in an state of FIG. 6, stress of the back-side band elastic member 35*b* in both the end parts BDe in the lateral direction of the back-side band member 30*b* results in being greater than stress of the abdominal-side band elastic member 35*a* in both the end parts ADe in the lateral direction of the abdominal-side band member 30*a*. This is because, in such corresponding parts, the back-side band elastic member 35*b* stretches greater than the abdominal-side band elastic member 35*a*. When stress is different between the abdominal side and the back side, deformation created in the band members 30*a*, 30*b* is different in size, resulting in deformation being greater on the abdominal side, on which stress is smaller. That is, the deformation on the front (abdominal side) of the diaper 1 results in wrinkles greater than that on the back (back side), which becomes more visible, thereby facilitating the front/back judgment.

Further, with configurations of the abdominal-side band member 30a and the back-side band member 30b according to an embodiment of the present disclosure, following effects can also be achieved when the diaper 1 is worn.

Figure 7:
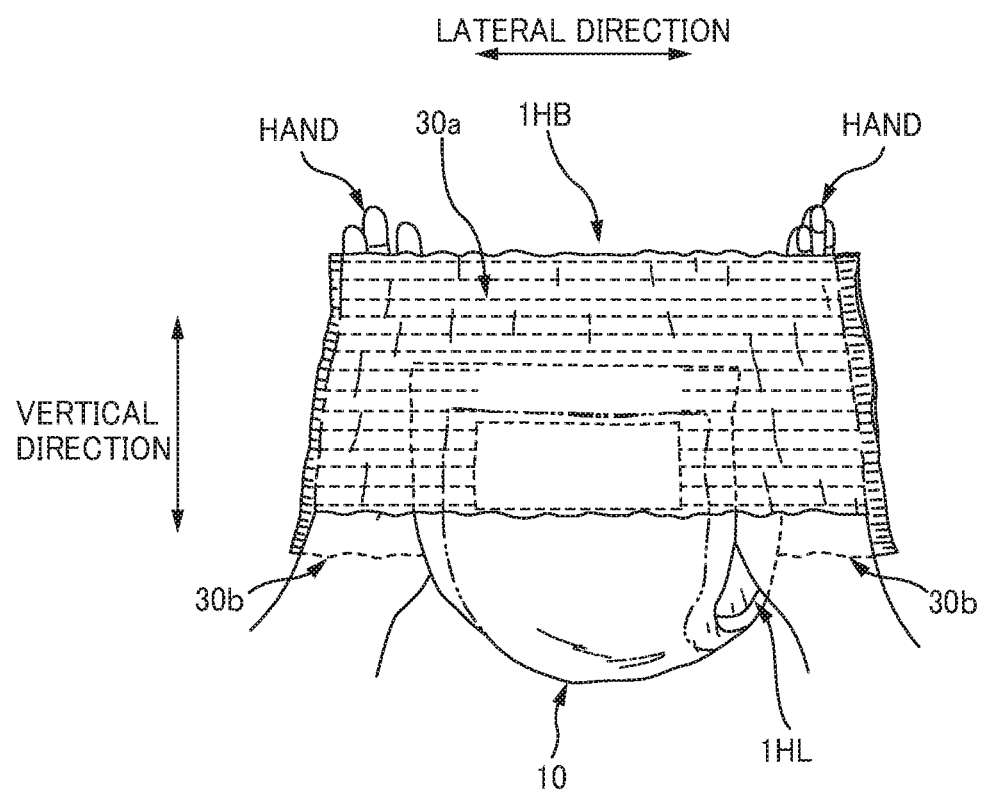
FIG. 7 is a diagram illustrating an action when having a diaper 1 to be worn.

FIG. 7 is a diagram illustrating an action when putting the diaper 1 on. When putting the diaper 1 on an infant or the like, first, one (corresponding to a user as described above) who diapers him/her or the like inserts one's hands into the pair of leg openings 1HL, 1HL formed on both ends in the lateral direction of the diaper 1, respectively, from the lower side in the vertical direction, and then stretch the abdominal-side band member 30a and the back-side band member 30b so as to extend them outward in the lateral direction, thereby expanding the waist opening 1HB as in FIG. 7. Thereafter, the one inserts legs of one who is to wear (hereinafter, also referred to as a wearer, e.g., an infant or the like, which may be an animal other than a human being) from the waist opening 1HB, pulls out the legs from the pair of the openings 1HL, 1HL, respectively, and then hitches up the diaper 1 to the wearer's waist part along the wearer's legs, thereby putting the diaper 1 thereon.

In such a series of operations, the one who puts the diaper 1 thereon is intended to hold a state in which the band members 30a, 30b are expanded in the lateral direction as illustrated in FIG. 7. In an embodiment of the present disclosure, since the area of the back-side band member 30b is larger, the area of contact between the back-side band member 30b and the backs of the hands results in being larger. That is, the backs of the hands tend to lie on the back-side band member 30b in a wide range, thereby causing a force thereof to be easily transferred when the band members 30a, 30b are extended in the lateral direction. Thus, the diaper 1 can be expanded in the lateral direction without effort. As a result, an action of putting the diaper 1 thereon can more easily be performed. Especially, as in an embodiment of the present disclosure, in a case where the back-side band elastic member 35b is disposed with stretchability provided over the entire region in the lateral direction of the back-side band member 30b, a force to expand the back-side band member 30b in the lateral direction results in being greater. Thus, the area of the back-side band member 30b is made larger as described above, so that the force of the hands can more easily be transferred in the back side, thereby being able to efficiently perform the action of putting the diaper 1 thereon.

Further, in a common three-piece type diaper, in a case where one or more elastic members are provided over the whole area in the lateral direction of the front and back band members, a tightening force when the diaper 1 is worn becomes greater. Thus, the diaper 1 easily digs into a wearer's skin, and as a result a mark is easily left by the elastic members. However, in the diaper 1 according to an embodiment of the present disclosure, since the area of the back-side band member 30b is made larger, the tightening force, which is provided by the elastic members, is spread thereover, so that a mark is not likely to be left in the wearer's skin.

Further, in the diaper 1, the area of the back-side band member 30b is made larger in the band members 30a, 30b to form "buttock cover", resulting in a configuration with which an infant or the like can be diapered more safely. As described above, when putting the diaper 1 thereon, one is directed to insert a wearer's legs from the waist opening 1HB into the leg openings 1HL. If the diaper 1 includes the abdominal-side band member 30a having a large area, and the abdominal-side band member 30a has portions configured to extend downward outside in the vertical direction, the wearer's fingers may easily be caught by such extending portions of the abdominal-side band member 30a, when the wearer's (infant or the like's) legs are inserted through the leg openings 1HL. However, with a configuration of the diaper 1 according to an embodiment of the present disclosure, not the abdominal-side band member 30a but the back-side band member 30b extends downward in the vertical direction. Accordingly, the fingers of the legs are less likely to be caught when putting the diaper 1 thereon, and thus, it becomes possible to diaper a wearer more safely.

Further, in the diaper 1 according to an embodiment of the present disclosure, the positional relationship between the absorbent main body 10 (absorbent core 11) and the abdominal-side and back-side band members 30a and 30b is adjusted, to differentiate touches when a user touches the diaper 1. Specifically, a distance (length in the vertical direction of AU in FIG. 5A) between an end on one side in the vertical direction of the absorbent main body 10 and the upper-edge part 30aet in the vertical direction of the abdominal-side band member 30a is smaller than a distance (length in the vertical direction of BU in FIG. 5B) between an end on the other side in the vertical direction of the absorbent main body 10 and the upper-edge part 30bet in the vertical direction of the back-side band member 30b. In this case, a distance (BU) from the upper-edge part 30bet to the upper end of the absorbent main body 10 is longer in the back-side band member 30b. Thus, when a user tries to hold the end part region on the back side of the waist opening 1HB in the diaper 1, the user touches the back-side band member 30b, but is less likely to touch the absorbent main body 10. Thus, on the back (back side) of the diaper 1, the user feels thin and soft to the touch of the back-side band member 30b. On the other hand, in the abdominal-side band member 30a, a distance (AU) from the upper-edge part 30aet to the upper end of the absorbent main body 10 is shorter. Thus, when a user tries to hold the end part region on the abdominal side of the waist opening 1HB in the diaper 1, the user is more likely to touch the absorbent main body 10 together with the abdominal-side band member 30a. Thus, on the front (abdominal side) of the diaper 1, the user feels thick and slightly hard to the touch of the abdominal-side band member 30a and the absorbent main body 10 (absorbent core 11).

As such, the positional relationship between the absorbent main body 10 and the band members 30a, 30b is adjusted to differentiate touches of the diaper 1 between the front and the back, thereby facilitating the front/back judgment, not only by sight but also touch. Note that, in an example described above, the length in the vertical direction of AU is smaller than the length in the vertical direction of BU (AU<BU). However, an equivalent effect can be achieved even if the length in the vertical direction of AU is made greater than the length in the vertical direction of BU (AU>BU). However, with AU<BU being satisfied, the area in which the absorbent main body 10 covers a wearer's abdominal side (front side) is made greater, thereby being able to more easily absorb urine.

Further, in the diaper 1 according to an embodiment of the present disclosure, it is possible to restrain uncomfortable touch on the buttock side caused by the aftertreatment tape 50 when the diaper is worn. In the diaper 1, an overlap portion where the back-side band member 30b and the absorbent main body 10 overlap each other in the vertical direction (BD in FIG. 3) is larger. This allows the aftertreatment tape 50 fixed to the non-skin side surface of the back-side band member 30b to easily overlap in position with the absorbent core 11 with respect to the thickness direction. When a wearer wears the diaper, the absorbent core 11 having an enough thickness in the thickness direction exists between the wearer's skin (buttocks) and the aftertreatment tape 50, such that the absorbent core 11 functions as a cushion. Thus, uncomfortable touch caused by the aftertreatment tape 50 is less likely to be conveyed to the wearer's skin (buttocks), thereby restraining uncomfortable feel.

===Other Embodiments===

Hereinabove, an embodiment according to the present disclosure have been described, and an embodiments described above are intended to facilitate the understanding of the present disclosure but not to limit the disclosure. And it is needless to say that modifications and improvements of the present disclosure are possible without departing from the scope of the disclosure, and equivalents thereof are also encompassed by the disclosure. For example, following modifications are possible.

In an embodiment described above, the elastic member(s) 35a is (are) provided with a disconnected part in the central portion ADc in the lateral direction of the lower region AD in the abdominal-side band member 30a, thereby causing stretchability (elasticity) to be less likely to act on the region. Then, by way of an example of an arrangement of such an elastic member, as illustrated in FIG. 3, such a configuration is given, in which the elastic members 35a exist in both the end parts ADce, ADce in the lateral direction in the central portion ADc, while the elastic members 35a do not exist in the central part ADcc in the lateral direction in the central portion ADc. However, it is not limited thereto.

Figure 8:
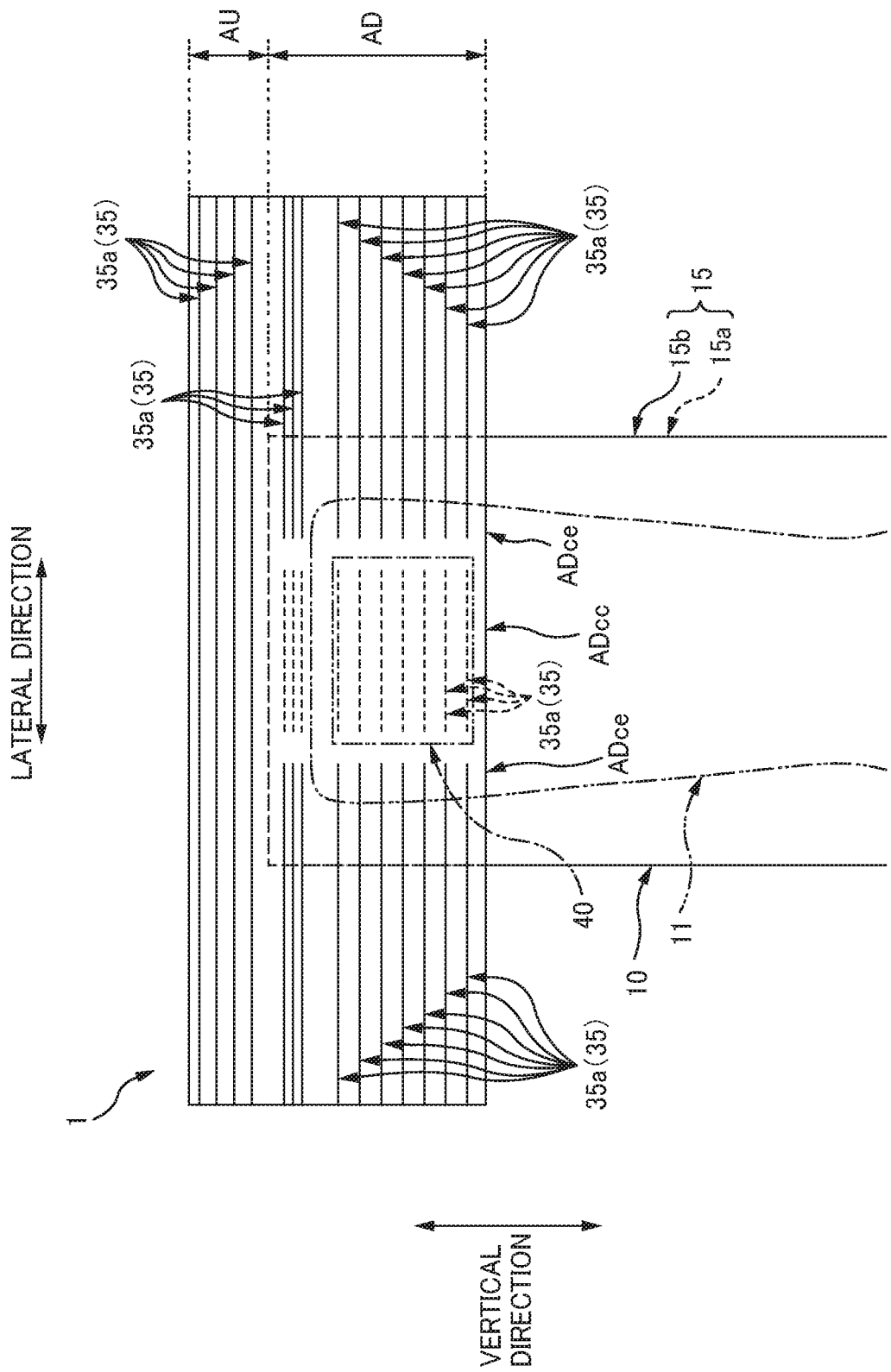
FIG. 8 is a schematic plan view illustrating an example in which an elastic member 35 exists in a central portion ADcc.

That is, the elastic member (s) 35a may exist in the central part ADcc in the central portion ADc, as long as the elastic member (s) 35a is arranged in a disconnected manner in the central portion ADc in the central portion ADc of the lower region AD. FIG. 8 is a schematic plan view illustrating such an example. Note that FIG. 8 illustrates a state in which the elastic members 35a are exposed to the exterior, while the nonwoven fabric 31 on the non-skin side in the abdominal-side band member 30a is removed. In this example in FIG. 8, the elastic members 35a located in the central part ADcc each have a plurality of disconnected parts, in such a state as to be divided into small parts. Then, when in such a chopped state, the elastic members 35a substantially do not provide stretchability to the central part ADcc. Accordingly, the elastic members 35a may exist in the central part ADcc, as long as in such a chopped state. The elastic member 35a in a chopped state has parts each having a length, e.g., larger than 0 mm and smaller than or equal to 5 mm, and in some embodiments, each length larger than 0 mm and smaller than or equal to 3 mm.

Figure 9:
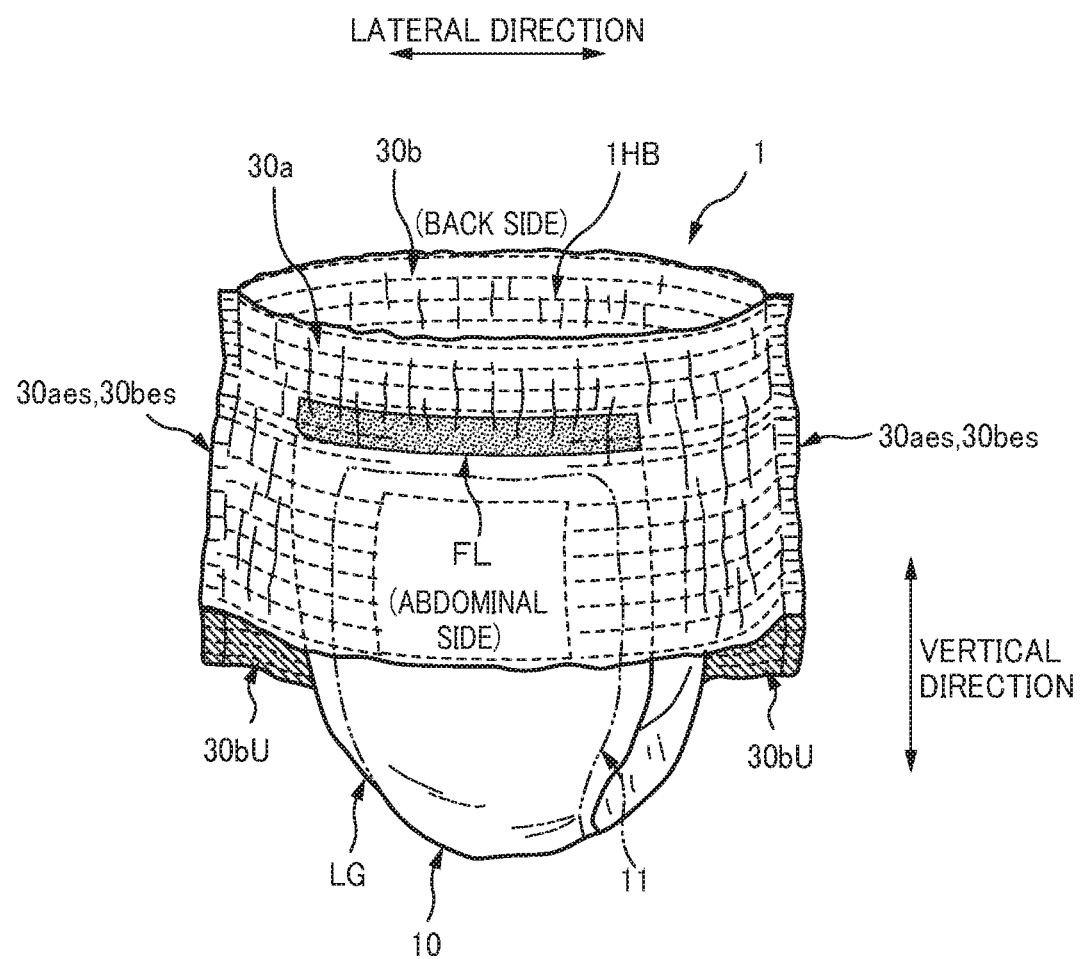
FIG. 9 is a schematic diagram illustrating an example of a diaper 1 when a color of a predetermined area is changed.

In an embodiment described above, the "color" of members of the absorbent main body 10, etc., configuring the diaper 1 has not been described, but the color of a predetermined area in members may be changed. FIG. 9 is a schematic diagram illustrating an example of the diaper 1 when the color of a predetermined area is changed. As illustrated with a shaded area FL in FIG. 9, the color of an area on the upper end in the vertical direction on the abdominal side of the absorbent main body 10 is changed. Specifically, a part of the upper end portion (abdominal side) in the vertical direction of the rear-surface sheet member 15, which is provided on the non-skin side in the thickness direction, in the members configuring the absorbent main body 10, is colored with a color (e.g., blue) different from that of other regions. Accordingly, a blue line along the upper end of the absorbent main body 10 can be seen through the abdominal-side band member 30a. Thus, it becomes more easily recognized that the side on which the line is visible is the front side (abdominal side) of the diaper 1. Note that the "color", with which the corresponding part is colored, is to be eye-catching, so that the line as above can be recognized. Further, the member may be not colored but a colored member may be provided. For example, in an example described above, a colored band-like member may be attached to the upper end portion (abdominal side) in the vertical direction of the rear-surface sheet member 15. Further, the upper end portion in the vertical direction of the absorbent main body 10 on the back side is colored with a color (e.g., orange) different from the color on the abdominal side, so that the color of the front is made different from the color of the back, thereby facilitating front/back judgment.

Further, the color of a part of the back-side band member elastic body 35b provided to the back-side band member 30b may be changed. In FIG. 9, the color of the back-side band member elastic body 35b disposed to a portion, which is not overlapping with the abdominal-side band member 30a, in the back-side band member elastic body 35b disposed to the lower region BU of the back-side band member 30b, is different from the color of the abdominal-side band member elastic body 35a disposed to the abdominal-side band member 30a. That is, the color of the back-side band member elastic body 35b provided to a portion extending on the lower side in the vertical direction with respect to the abdominal-side band member 30a is changed. When the diaper 1 is viewed from the front side, the color of the back-side band member elastic body 35b is seen in both the end parts in the lateral direction (areas corresponding to the extending areas 30bu in FIG. 5A), as indicated by the shaded areas in FIG. 9, and the color of the absorbent main body 10 is seen in the central portion in the lateral direction. On the other hand, when the diaper 1 is seen from the back side, the color of the back-side band member elastic body 35b is seen as a band-like region that is continuous in the lateral direction near the lower end in the vertical direction of the back-side band member 30b (not shown) . Such a configuration also facilitates clear judgment between the front and the back of the diaper 1.

In an embodiment described above, each of the materials of the exterior sheet 15b and the abdominal-side and back-side band members 30a, 30b is a nonwoven fabric, but the material is not limited to the nonwoven fabric. For example, it may be a woven fabric, or a sheet member other than the woven fabric. The exterior sheet 15b may be omitted and, in such a case, the leak-proof sheet 15a results in the exterior of the absorbent main body 10.

In an embodiment described above, a rubber thread is given as an example of the elastic member 35, but it is not limited thereto. For example, band-like rubber may be used as the elastic member 35. Further, a band-like nonwoven fabric having stretchability and/or a band-like resin film having stretchability may be used.

REFERENCE SIGNS LIST 1 diaper (absorbent article), 1HB waist opening, 1HL leg opening,
10 absorbent main body, 10ea end part, 10eb end part,
10es end part, 10p portion,
11 absorbent core,
11a abdominal-side end part, 11b back-side end part,
11c constriction,
13 surface sheet member,
15 rear-surface sheet member,
15a leak-proof sheet, 15b exterior sheet,
15bf extending portion, 15bg folded portion, 17 leg elastic member, 18 LSG elastic member,
19 leg auxiliary elastic member,
30a abdominal-side band member, 30ac central portion,
30ac2 part,
30aes side-edge part, 30ae2 end part, 30aet upper-edge part,
30b back-side band member, 30bc central portion, 30bc2 part,
30bes side-edge part, 30be2 end part, 30bet upper-edge part,
30bu extending area,
31 nonwoven fabric, 32 nonwoven fabric,
35 elastic member,
35a abdominal-side band elastic member,
35b back-side band elastic member,
40 illustration sheet,
50 aftertreatment tape,
AU upper region, AD lower region,
ADc central portion, ADcc central part, ADce end part,
ADe part,
FL shaded area,
LG leg gathers,
LSG leg side-gathers (leakage-proof wall part),
LSGb base end part, LSGf free end part,

The invention claimed is:

1. An absorbent article having a vertical direction and a lateral direction intersecting the vertical direction, the absorbent article comprising:
   an absorbent main body provided along the vertical direction and configured to absorb excreta;
   an abdominal-side band member provided along the lateral direction, the abdominal-side band member having a central portion in the lateral direction fixed to one end part of the absorbent main body in the vertical direction, while covering the one end part from a non-skin side of the absorbent main body; and
   a back-side band member provided along the lateral direction as a member different from the abdominal-side band member, the back-side band member having a central portion in the lateral direction fixed to an other end part of the absorbent main body in the vertical direction, while covering the other end part from the non-skin side of the absorbent main body,
   wherein
   the back-side band member has a length in the vertical direction longer than a length of the abdominal-side band member in the vertical direction,
   each of the abdominal-side band member and the back-side band member has an elastic member disposed thereto along the lateral direction, the elastic member being configured to expand and contract along the lateral direction,
   the abdominal-side band member and the absorbent main body overlap each other at an abdominal-side overlap portion, the abdominal-side overlap portion including at least a part where the elastic member of the abdominal-side band member is disconnected,
   the back-side band member has a substantially rectangular shape in a plan view,
   the elastic member of the back-side band member continuously extends in the lateral direction, and
   the elastic member of the abdominal-side band member discontinuously extends in the lateral direction.

2. The absorbent article according to claim 1, wherein
a length from an end on one side of the absorbent main body in the vertical direction to an upper end of the abdominal-side band member in the vertical direction is different from a length from an end on an other side in the vertical direction of the absorbent main body to an upper end of the back-side band member in the vertical direction.

3. The absorbent article according to claim 1, wherein
the absorbent main body includes an absorbent core including a liquid absorbent material stacked in a predetermined thickness,
the central portion of the abdominal-side band member has a first area where the absorbent core is not disposed, the first area overlapping with the absorbent main body, the first area including at least the part where the elastic member is disconnected,
the central portion of the abdominal-side band member has a second area where the absorbent core is disposed, the second area overlapping with the absorbent main body,
the second area including at least the part where the elastic member is disconnected,
the central portion of the abdominal-side band member has a third area not overlapping with the absorbent main body, the third area being in a region where the elastic member is disposed in a state stretched over between one end side and an other end side thereof in the lateral direction,
the first area is between the second and third areas, and
in a state that the absorbent main body is two-folded at a central part thereof in the vertical direction and side-edge parts of the abdominal-side band member in the lateral direction are coupled to side-edge parts of the back-side band member in the lateral direction, respectively, an upper end of the abdominal-side band member in the vertical direction is different in position in the vertical direction from an upper end of the back-side band member in the vertical direction.

4. The absorbent article according to claim 1, wherein
the length of the back-side band member in the vertical direction is longer than a half of a length in the vertical direction of the absorbent article in the vertical direction in a state that the absorbent main body is two-folded at a central part thereof in the vertical direction and side-edge parts of the abdominal-side band member in the lateral direction are coupled to side-edge parts of the back-side band member in the lateral direction, respectively.

5. The absorbent article according to claim 1, wherein
the back-side band member and the absorbent main body overlap each other at a back-side overlap portion, and
in a state that the absorbent main body is two-folded at a central part thereof in the vertical direction and side-edge parts of the abdominal-side band member in the lateral direction are coupled to side-edge parts of the back-side band member in the lateral direction, respectively,
a length between each end of the back-side overlap portion and an adjacent one of the side-edge parts of the back-side band member is longer than a length between each end of the abdominal-side overlap portion and an adjacent one of the side-edge parts of the abdominal-side band member.

6. The absorbent article according to claim 5, wherein
a stress of the elastic member disposed between the each end of the back-side overlap portion and the adjacent one of the side-edge parts of the back-side band member is greater than a stress of the elastic member disposed between the each end of the abdominal-side overlap portion and the adjacent one of the side-edge parts of the abdominal-side band member.

7. The absorbent article according to claim 1, wherein in a state that the absorbent main body is two-folded at a central part thereof in the vertical direction and side-edge parts of the abdominal-side band member in the lateral direction are coupled to side-edge parts of the back-side band member in the lateral direction, respectively,
- the elastic member has at least a part disposed to a portion of the back-side band member and not overlapping the abdominal-side band member, and
- at least the part of the elastic member has a color different from a color of the elastic member disposed to the abdominal-side band member.

8. The absorbent article according to claim 1, wherein a dimension of the absorbent main body in the lateral direction in the back-side band member is shorter than in the abdominal-side band member.

9. The absorbent article according to claim 1, wherein
- the back-side band member has a continuous elastic panel defined by a portion of the elastic member in the back-side band member, and
- the abdomen-side band member has a discontinuous elastic panel defined by another portion of the elastic member in the abdomen-side band member.

10. An absorbent article having a vertical direction and a lateral direction intersecting the vertical direction, the absorbent article comprising:
- an absorbent main body provided along the vertical direction and configured to absorb excreta;
- an abdominal-side band member provided along the lateral direction, the abdominal-side band member having a central portion in the lateral direction fixed to one end part of the absorbent main body in the vertical direction, while covering the one end part from a non-skin side of the absorbent main body; and
- a back-side band member provided along the lateral direction as a member different from the abdominal-side band member, the back-side band member having a central portion in the lateral direction fixed to an other end part of the absorbent main body in the vertical direction, while covering the other end part from the non-skin side of the absorbent main body, wherein the back-side band member has a length in the vertical direction longer than a length of the abdominal-side band member in the vertical direction, each of the abdominal-side band member and the back-side band member has an elastic member disposed thereto along the lateral direction, the elastic member being configured to expand and contract along the lateral direction, the abdominal-side band member and the absorbent main body overlap each other at an abdominal-side overlap portion, the abdominal-side overlap portion including at least a part where the elastic member of the abdominal-side band member is disconnected, the back-side band member has a substantially rectangular shape in a plan view, the absorbent main body includes an absorbent core including a liquid absorbent material stacked in a predetermined thickness, the central portion of the abdominal-side band member has a first area where the absorbent core is not disposed, the first area overlapping with the absorbent main body, the first area including at least the part where the elastic member is disconnected, the central portion of the abdominal-side band member has a second area where the absorbent core is disposed, the second area overlapping with the absorbent main body, the second area including at least the part where the elastic member is disconnected, the central portion of the abdominal-side band member has a third area not overlapping with the absorbent main body, the third area being in a region where the elastic member is disposed in a state stretched over between one end side and an other end side thereof in the lateral direction, the first area is between the second and third areas, and in a state that the absorbent main body is two-folded at a central part thereof in the vertical direction and side-edge parts of the abdominal-side band member in the lateral direction are coupled to side-edge parts of the back-side band member in the lateral direction, respectively, an upper end of the abdominal-side band member in the vertical direction is different in position in the vertical direction from an upper end of the back-side band member in the vertical direction.

* * * * *